US008712583B2

(12) United States Patent
Madris et al.

(10) Patent No.: US 8,712,583 B2
(45) Date of Patent: *Apr. 29, 2014

(54) AUTOMATIC PILL DISPENSER

(71) Applicant: Innovative Dispensing, LLC, Miami Beach, FL (US)

(72) Inventors: Russell Madris, Miami Beach, FL (US); Travis Cochran, Fountain Valley, CA (US); Bert Centala, Fountain Valley, CA (US)

(73) Assignee: Innovative Dispensing, LLC, Miami Beach, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/848,948

(22) Filed: Mar. 22, 2013

(65) Prior Publication Data

US 2013/0282170 A1 Oct. 24, 2013

Related U.S. Application Data

(63) Continuation of application No. 13/451,525, filed on Apr. 19, 2012, now Pat. No. 8,452,446.

(51) Int. Cl.
*B65D 83/04* (2006.01)
*G06F 17/00* (2006.01)
*B65H 3/60* (2006.01)
*B65H 1/00* (2006.01)

(52) U.S. Cl.
USPC ........... 700/236; 700/237; 700/241; 700/240; 700/244

(58) Field of Classification Search
USPC .......... 221/200, 204, 205, 133; 700/232, 236, 700/241–243, 237, 240, 244
See application file for complete search history.

(56) References Cited

U.S. PATENT DOCUMENTS

| | | | |
|---|---|---|---|
| 6,732,884 B2 * | 5/2004 | Topliffe et al. ..................... 221/3 |
| 8,452,446 B1 * | 5/2013 | Madris et al. ................. 700/236 |
| 8,521,326 B1 * | 8/2013 | Holtje ............................ 700/242 |
| 2004/0155049 A1 * | 8/2004 | Float et al. ....................... 221/12 |
| 2010/0018986 A1 * | 1/2010 | Kodama et al. ................... 221/8 |
| 2011/0303692 A1 * | 12/2011 | Kim ................................. 221/1 |
| 2013/0282170 A1 * | 10/2013 | Madris et al. ................. 700/236 |

* cited by examiner

*Primary Examiner* — Michael K Collins
(74) *Attorney, Agent, or Firm* — Cotman IP Law Group, PLC

(57) ABSTRACT

A pill dispensing device includes a base with a top surface and a bottom surface, a transfer tray assembly coupled to the top surface of the base, a controller, and a plurality of vibrating tray assemblies. Each vibrating tray assembly couples to the top surface of the base and includes a pill tray, at least one spring support, a pill tray electric motor, and at least one optical sensor. The pill tray has an open end which is positioned above the transfer tray assembly. The at least one spring support is coupled between the top surface of the base and the pill tray. The pill tray electric motor couples to the pill tray and an offset weight. Each pill tray electric motor electrically couples to the controller. An optical sensor couples to the pill tray.

16 Claims, 4 Drawing Sheets

AUTOMATIC PILL DISPENSER

CROSS-REFERENCE TO RELATED APPLICATIONS

This application is a continuation of U.S. patent application Ser. No. 13/451,525, filed Apr. 19, 2012, the contents of which is hereby incorporated by reference in its entirety.

BACKGROUND OF THE INVENTION

1. Field of the Invention

The present invention relates pill dispensers, and more specifically, to an automatic pill dispenser that dispenses the correct amount and types of medications and supplements at specified times and dates.

2. Description of the Related Art

Medications, vitamins, supplements in the forms of pills and capsules are typically provided in plastic containers with twist-off caps. A user typically ingests multiple pills of different types at specific times as according to the user's medical prescription or supplement needs. The task of manually opening each plastic container, extracting the correct number of pills, then closing the container again for a number of different containers is not only time consuming, but also tiring and requires mental focus. It is not uncommon for a user to make mistakes in extracting the desired number of pills from a plurality of plastic containers. This is an exacerbated problem for users who are suffering from memory loss or other mental impairments or users who have arthritis or other physical impairments.

A number of devices have been developed for automatically dispensing pills. U.S. Pat. No. 7,359,765 discloses an electronic pill dispenser includes a container and a cap removably attached to the container. Components of the pill dispenser include a power source, pill dispenser circuitry, a real time clock, a counter, a display, a dispensing mechanism, a sensor, a visual indicator, an audible indicator, an input/output interface, an input output port, and a communication bus electrically interconnecting the components.

U.S. Pat. No. 6,427,865 discloses a device and method for dispensing pills or vitamins is disclosed which includes a rotatable chamber within a housing. The chamber contains multiple slots for storing the pills or vitamins, and the housing has at least one dispensing hole so that pills will fall from the containment slot when it is aligned with the hole. The chamber may be rotated by motorized or manual means, with the preferred motorized means being an electric motor connected to a worm drive that engages gear teeth along the edge of the chamber, and the preferred mechanical means being a handle with a hinged tab.

None of these disclosures, either individually or in combination, discloses the features of the present invention as claimed.

BRIEF SUMMARY OF THE INVENTION

Accordingly, the present invention provides for an effective device which is capable of quickly and accurately dispensing the correct amount and types of medications and supplements at specified times and dates. The present invention saves user time and avoids the health risks from taking inaccurate dosages of medications and supplements.

A pill dispensing device includes a base with a top surface and a bottom surface, a transfer tray assembly coupled to the top surface of the base, a controller, and a plurality of vibrating tray assemblies. Each vibrating tray assembly couples to the top surface of the base and includes a pill tray, at least one spring support, a pill tray electric motor, and at least one optical sensor. The pill tray has an open end which is positioned above the transfer tray assembly. The at least one spring support is coupled between the top surface of the base and the pill tray. The pill tray electric motor couples to the pill tray and an offset weight. Each pill tray electric motor electrically couples to the controller. At least one optical sensor couples to the pill tray.

A user configures the controller using the input interface and the visual display to execute a specified pill setting and/or a specified dispensing schedule. A different type of pill is then loaded into each of at least one pill tray of the pill dispensing device. The pill dispensing device will then proceed to dispense pills according to the specified pill setting and/or the specified dispensing schedule.

These and other aspects of the present invention will become more fully understood upon further review of the following specifications and accompanying drawings.

BRIEF DESCRIPTION OF THE DRAWINGS

The above and other aspects, features and advantages of the invention will be more apparent from the following more particular description thereof, presented in conjunction with the following drawings wherein.

DETAILED DESCRIPTION

A pill dispensing device will now be described. In the following exemplary description numerous specific details are set forth in order to provide a more thorough understanding of embodiments of the invention. It will be apparent, however, to an artisan of ordinary skill that the present invention may be practiced without incorporating all aspects of the specific details described herein. In other instances, specific features, quantities, or measurements well known to those of ordinary skill in the art have not been described in detail so as not to obscure the invention. Readers should note that although examples of the invention are set forth herein, the claims, and the full scope of any equivalents, are what define the true scope of the invention.

Figure 1:
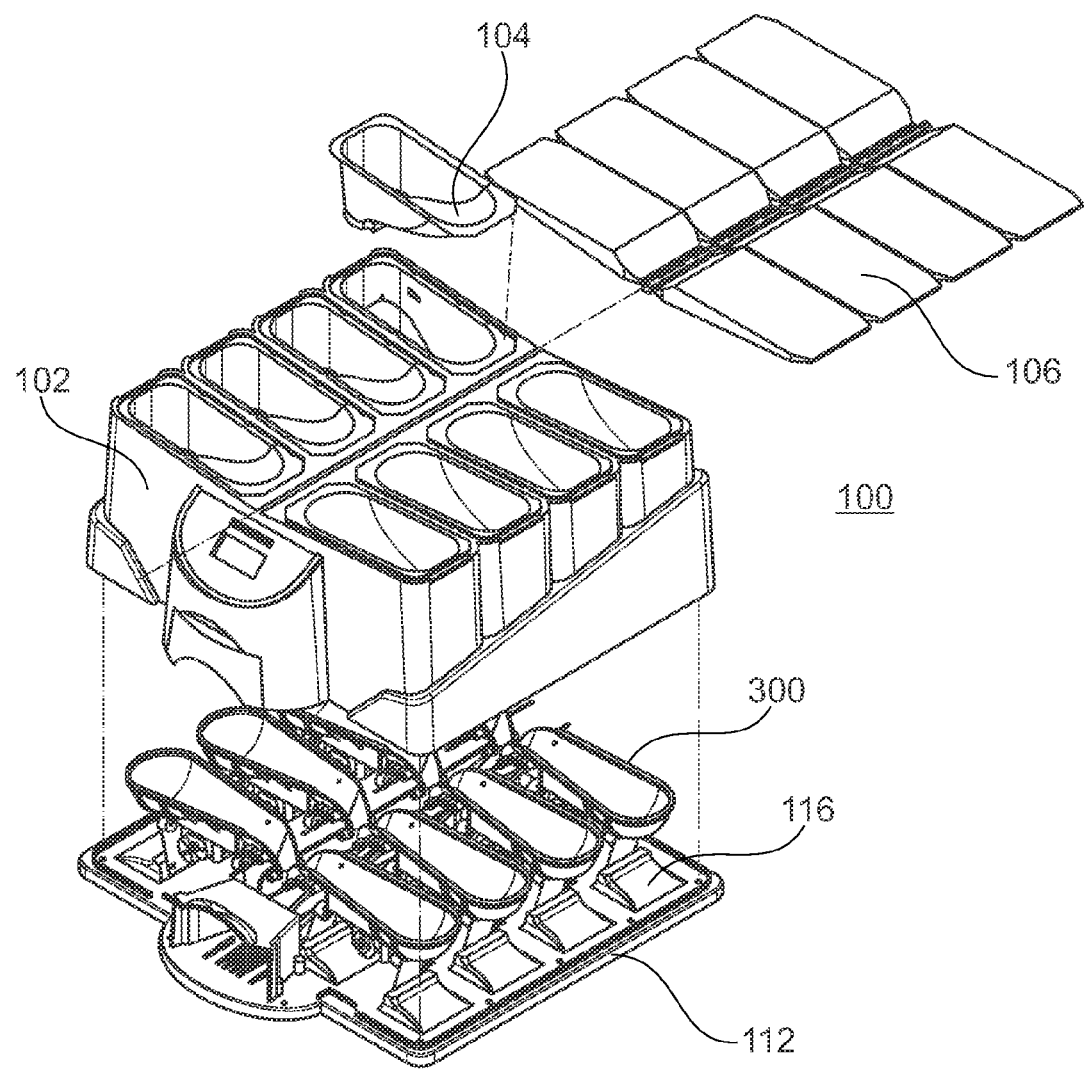
FIG. 1 illustrates an exploded view of an exemplary pill dispensing device in accordance with an embodiment of the present invention.

FIG. 1 illustrates an exterior view of an exemplary pill dispensing device 100 in accordance with an embodiment of the present invention. An enclosure body 102 couples to a base 112, a closable lid 106, and a plurality of hoppers 104. The closable lid 106 is substantially rectangular planar shaped and include a plurality of substantially rectangular planar shaped independently closable sections. For example, in one embodiment, the lid 106 includes 8 independently closable sections. In one configuration, 4 closeable sections line up to form a first column and another 4 closeable sections line up to form a second column coupled to the first column at a central lid spine. Each closable section is coupled by a hinge to the rest of the lid 106 at the central lid spine and is capable of rotational displacement along an axis defined by the central lid spine. In some embodiments, the closable lid 106 includes an ultraviolet resistant material. The ultraviolet resistant material may be any material resistant to the penetration of ultraviolet light.

The enclosure body 102 is substantially rectangular box shaped. In one configuration, the enclosure body 102 has an open bottom side and a partially open top side. For example, the top side of the enclosure body 102 in FIG. 1 has 8 openings, matching the number of independently closable sections of the lid 106. Each of the 8 openings is located substantially under a corresponding independently closable section of the lid 106. The central lid spine is coupled to a central line at the top side of the enclosure body 102. The bottom side of the enclosure body 102 is coupled to an outer perimeter of the base.

In the example shown in FIG. 1, the enclosure body 102 is coupled to 8 hoppers 104 at the 8 openings of the top side of the enclosure body 102. Each hopper 104 is shaped to function as a funnel with a larger top side opening and a smaller bottom side opening. The top side opening of each hopper 104 is substantially equally sized and shaped as each opening of the top side of the enclosure body 102.

Figure 2:
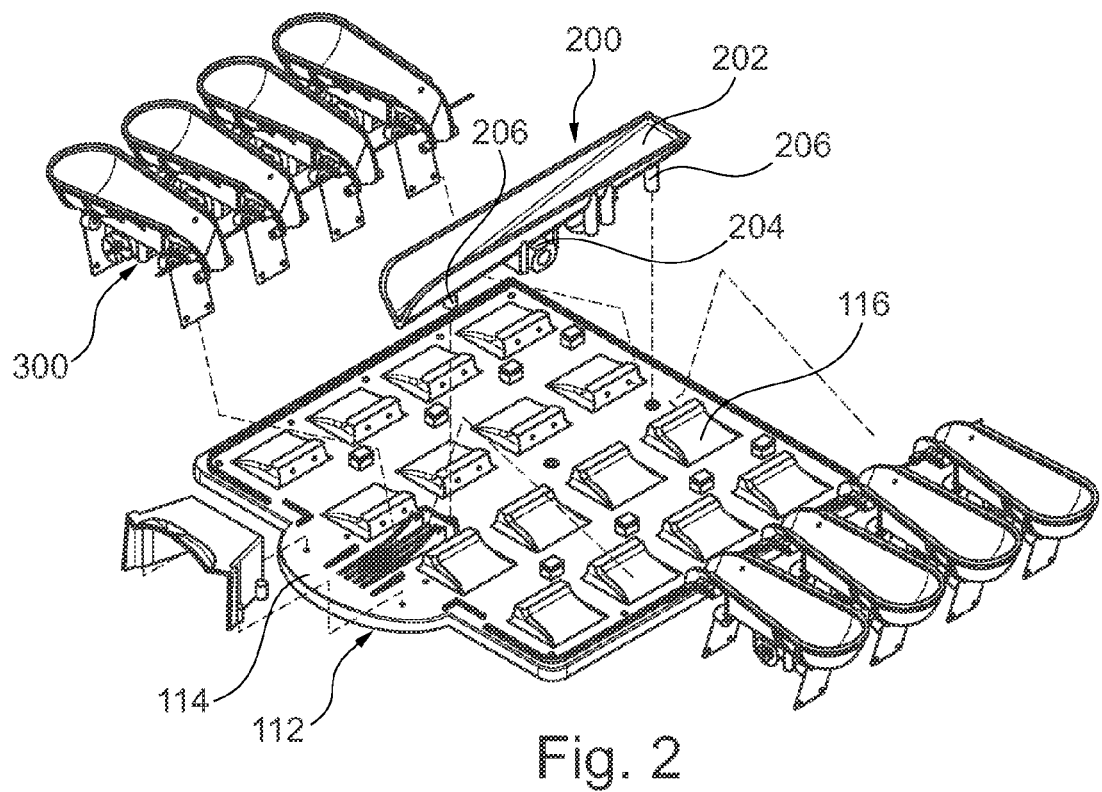
FIG. 2 illustrates an exploded interior view of an exemplary pill dispensing device in accordance with an embodiment of the present invention.

FIG. 2 illustrates an exploded interior view of an exemplary pill dispensing device 100 in accordance with an embodiment of the present invention. The base 112 is substantially flat and has a top surface, a bottom surface, a front 114, and a rear. 8 vibrating tray assemblies 300 couples to the base 112.

Figure 3:
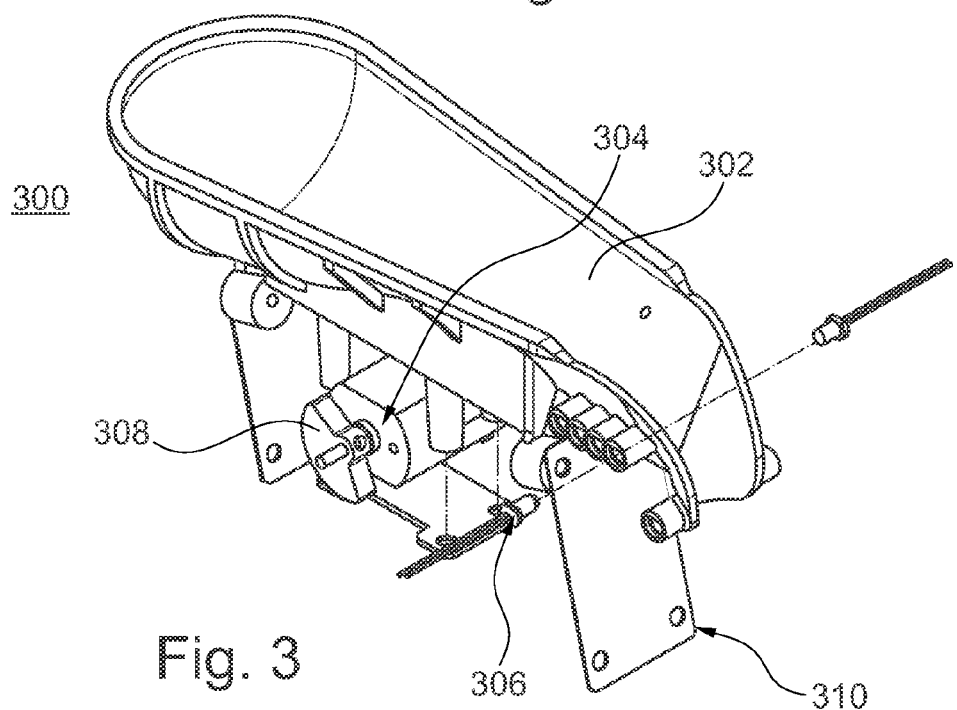
FIG. 3 illustrates a vibrating tray assembly of an exemplary pill dispensing device in accordance with an embodiment of the present invention.

FIG. 3 illustrates a vibrating tray assembly 300 of an exemplary pill dispensing device 100 in accordance with an embodiment of the present invention. Each vibrating tray assembly 300 comprises at least one spring support 310, a pill tray 302, a pill tray electric motor 304, and at least one optical sensor 306. The spring support 310 is substantially rectangular plate shaped. A spring support 310 is coupled to each protrusion 116 of the bottom surface of the base 112 at slightly non-perpendicular angle to the bottom surface of the base 112. The spring support 310 may comprise any combination of metals, plastic polymers, rubber, or other suitable materials allowing controlled vibration of the vibrating tray assembly 300. In one embodiment, the pill tray 302 is trough shaped with an open end and a closed end and transitions from a smaller sized V-shaped cross section at the open end to a larger sized V-shaped cross section at the closed end. The pill tray 302 is coupled to two spring supports, with one spring support coupled closer to the open end of the pill tray and another spring support 310 coupled closer to the closed end of the pill tray. The length of the pill tray 302 is substantially parallel to the top surface of the base. The pill tray electric motor 304 is coupled to the pill tray 300 at a bottom surface of the pill tray 300. The pill tray electric motor 304 may have a drive shaft that is coupled to a pill tray offset weight 308. The pill tray offset weight 308 has a mass that is positioned off center from to the drive shaft to cause a vibrating motion on the pill tray 300 when the pill tray electric motor 304 creates rotational motion on the drive shaft. The shape of the pill tray and the angle of the at least one spring support are specifically configured to effectively allow the vibrating motion on the pill tray assembly to cause pills in the pill tray to move from the closed end to the open end of the pill tray in a single file formation.

Figure 4:
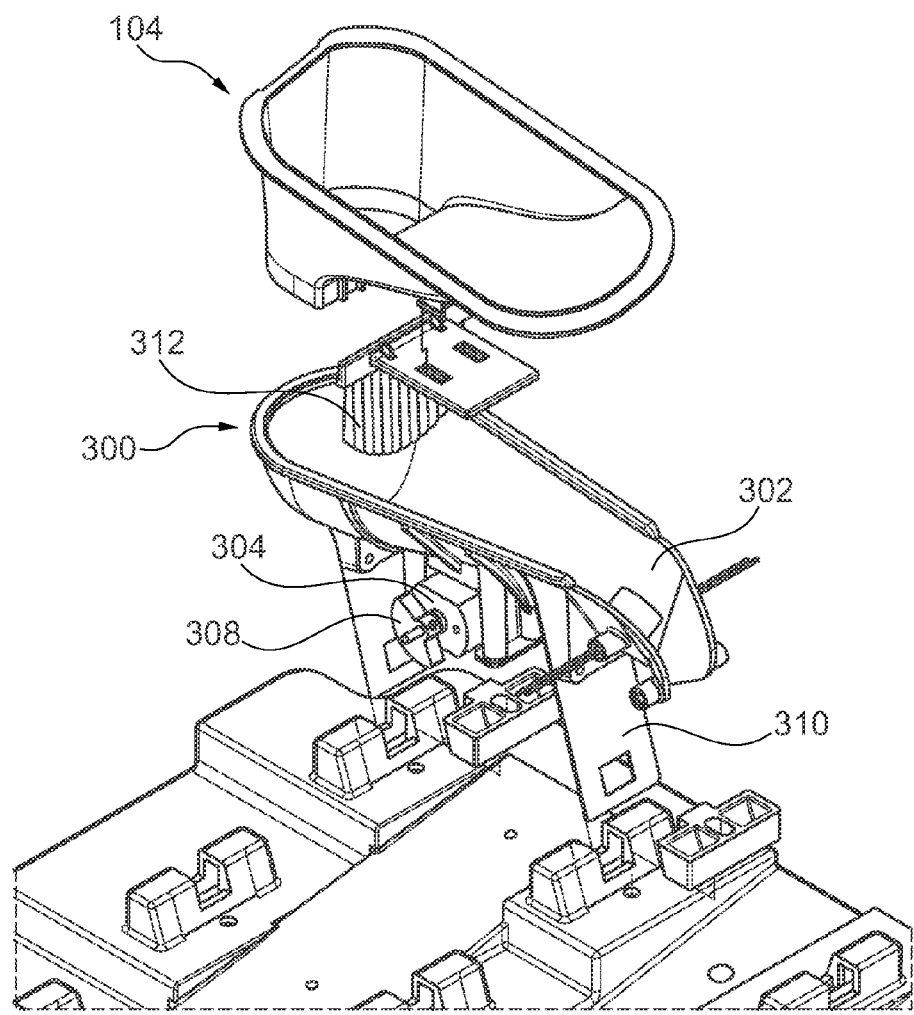
FIG. 4 illustrates an exploded view of a hopper, brush, and vibrating tray assembly of an exemplary pill dispensing device in accordance with an embodiment of the present invention.

FIG. 4 illustrates an exploded view of a hopper, brush, and vibrating tray assembly of an exemplary pill dispensing device in accordance with an embodiment of the present invention. In some embodiments, a brush 312 including flexible bristles is coupled to each hopper 104 with the flexible bristles extending towards the pill tray 302. Pills must move between the flexible bristles to travel from the hopper 104 to the open end of the pill tray. The thickness, material, and density of the flexible bristles affect the rate that pills flow from the hopper 104 to the pill tray 302. At least one optical sensor 306 couples to the pill tray 302 near the open end of the pill tray. In some embodiments, an approach optical sensor is configured to detect the presence of pills approaching the open end of the pill tray. A drop optical sensor is configured to detect whether a pill has dropped out of the pill tray 302. The optical sensors 306 may be an infrared sensor or any other sensor suitable for detecting the presence of objects.

A transfer tray assembly 200 has support posts 206 by which the transfer tray assembly 200 is coupled to the base 112. The length of the transfer tray assembly 200 is positioned below the open ends of the 8 pill trays 302. The transfer tray assembly 200 includes a transfer tray 202 that is trough shaped with an open end and a closed end. The transfer tray 202 cross-section is wider and shorter at the closed end and becomes narrower and taller towards the open end. In some embodiments, at least one transfer tray electric motor 204 is attached is coupled to the transfer tray 202 at a bottom surface of the transfer tray 202. The transfer tray electric motor 204 may have a drive shaft that is coupled to a transfer tray offset weight. The transfer tray offset weight has a mass that is positioned off center to the drive shaft to cause a vibrating motion on the transfer tray assembly 200. When the transfer tray electric motor 204 is turned on, pills in the transfer tray 202 will be shifted towards the open end of the transfer tray 202.

In one embodiment, the pill dispensing device 100 includes a controller, a visual display, and an input interface. The controller is configured to store at least one pill setting, where each pill setting causes the controller to dispense a specified number of each of at least one type of pill. Multiple pill settings facilitate the needs of multiple individuals with different pill needs who share use of the same device.

In some embodiments, the controller is configured to store at least one dispensing schedule, where each dispensing schedule causes the controller to dispense a specified number of each of at least one type of pill at specific times and dates. This facilitates the needs of multiple individuals who wish the correct number and types of pills to be automatically dispensed at specific times and dates. In some embodiments, the controller is configured to cause an audio output device to emit an audio reminder and/or cause a visual output device to emit a visual reminder at about the time at least one pill is automatically dispensed from the pill dispensing device 100 at the specific times and dates. The audio output device may be a speaker or any device for producing audible sound. The audio reminder may be an alarm sound, a musical note, song, or any other suitable sound. The visual output device may be a LCD display screen, LED lights, or any device for producing a visible cue. The visual reminder may be flashes of light or any other visible cue.

In some embodiments, the controller saves a record of a count of pills dispensed for each type of pill dispensed from the at least one type of pill stored in the pill dispenser device 100. The record may additionally include dates and times of the pills dispensed. This allows a user, family member, or caretaker to view the record of the user's pill intake.

In some embodiments, the pill dispensing device 100 is connected to a communication network. The communication network may be any means of digital communication such as the internet, a local area network, Bluetooth network, or a wireless network. A computer or a mobile device connected to the communication network may be used to remotely input a pill setting or a dispensing schedule. In some embodiments, the record of the user's pill intake may be viewed from the computer or the mobile device.

The pill tray stores a plurality of pills. The pill tray electric motor 304 causes the pill tray assembly 302 to vibrate which shifts the plurality of pills towards the open end of the pill tray 302. A pill's speed of travel is effectively controlled by pulsing the pill tray electric motor 304 on and off for varying lengths of time. Longer pulses allow the pills to achieve a higher speed while shorter pulses can cause the pills to be gently nudged forward. In some embodiments, the controller is configured to cause the pill tray electric motor to apply motor braking at an end of every motor pulse to more quickly stop the motor pulse. Each dispense cycle begins with one relatively short pulse just in case a small pill happens to be right at the very edge of the pill tray 302 near the open end and only needs a slight nudge to be dropped into the transfer tray 202, ending that cycle. The approach optical sensor and drop optical sensor are located near the point where pills are to drop from the pill tray onto the transfer tray 202. The approach optical sensor is used to sense that the pill is approaching the drop point and allows the pill tray electric motor 304 pulse time to be reduced, thereby reducing the speed of the pill in order to prevent more than one pill at a time from being dropped onto the transfer tray 202. The drop optical sensor is used to sense that the pill has actually dropped onto the transfer tray 202. The pill is counted only when sensed by the drop optical sensor. Following the first short pulse, combinations of medium to long pulses are applied until the approach optical sensor detects a pill. At that time the pill tray electric motor 304 is stopped and then very short pulses are applied to gently nudge the pills over the edge of the pill tray 302 and into the transfer tray 202.

Figure 5:
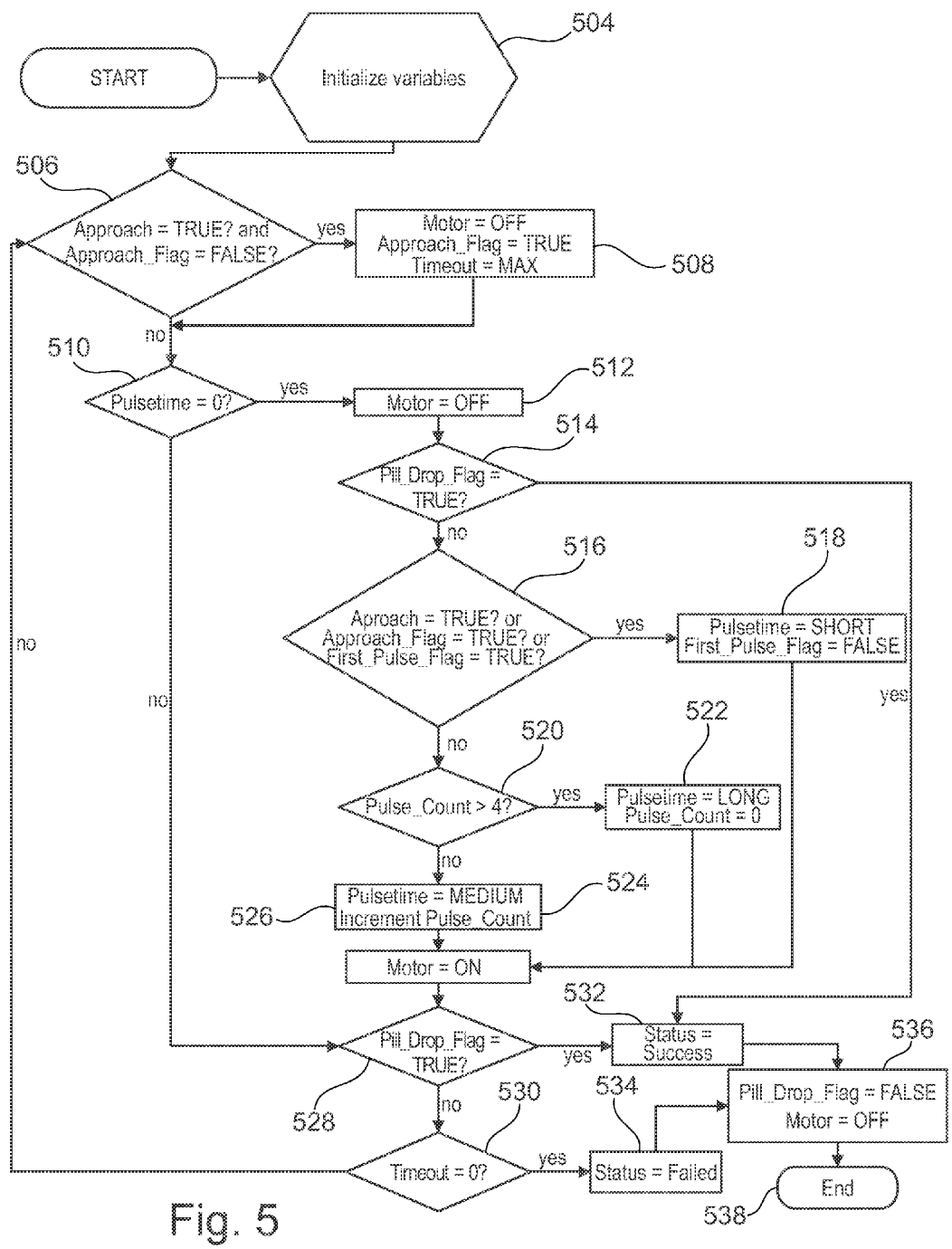
FIG. 5 illustrates a flow chart of a method of dispensing only one pill at a time in accordance with an embodiment of the present invention.

FIG. 5 illustrates a flow chart of a method of dispensing only one pill at a time in accordance with an embodiment of the present invention. In some embodiments, the controller will automatically execute software to dispense one pill at a time. The software may store a number of variables that are used in the control sequence. "Pulsetime" is a variable that indicates the time left to keep the pill tray electric motor on. The "Pulsetime" variable automatically decreases to 0 with time. "SHORT", "MEDIUM", and "LONG" are constants that are predetermined to be different lengths of time. The "First_Pulse_Flag" is a Boolean variable set to TRUE until the pill tray electric motor has been turned on once. "Motor" is a Boolean variable set to ON or OFF to indicate whether the pill tray electric motor is on or off. "Approach" is a Boolean variable which is normally set to FALSE and set to TRUE when the approach optical sensor detects a pill. "Approach_Flag" is a Boolean variable that is set to FALSE until the approach optical sensor detects a pill then set to TRUE thereafter. "Timeout" is a variable that indicates a time out length of time which is the time left until the process is abandoned as a failure. "Timeout" automatically decreases to 0 with time. "MAX" is a constant that is predetermined to be a time out length of time. "Pulse_Count" is a variable that indicates the number of times that the pill tray electric motor has been turned on then off "Pill_Drop_Flag" is a Boolean variable that is set to FALSE until the drop optical sensor detects a pill then set to TRUE thereafter.

The method begins by the controller initializing process variables at 504. For instance, Pulsetime is set to 0; First_Pulse_Flag is set to TRUE; Motor is set to OFF; Approach_Flag is set to FALSE; Timeout is set to MAX; Pulse_Count is set to 0; and Pill_Drop_Flag is set to FALSE.

To accurately dispense only one pill from pill tray 302, at step 506 the controller checks whether a pill is approaching the open end of the pill tray where the approach optical sensor is located, i.e. if the approach optical sensor has detected an approaching pill. If a pill is not detected by the approach optical sensor, the Approach discrete will be FALSE and processing will proceed to step 510. However, if at step 506, an approaching pill is detected, the Approach discrete will be set to TRUE and since the Approach_Flag was initialized to FALSE, processing will proceed to step 508 where the Motor discrete is set to OFF, Approach_Flag is set to TRUE, and Timeout variable is set to MAX. From step 508, processing proceeds to step 510.

At step 510, the controller checks the value of the Pulsetime variable. If the value of Pulsetime is not 0, processing proceeds to step 528. However, if the value of Pulsetime is 0 (e.g. value at initialization or after decreasing from a preset value over a period of time), the Motor discrete is set to OFF at step 512, i.e. the pill tray electric motor 304 is turned off, and processing proceeds to step 514. At step 514, the Pill_Drop_Flag status is checked to see if the drop optical sensor detected a pill. If the Pill_Drop_Flag is set to TRUE, this means that the pill has dropped and processing proceeds to step 532. However, if at step 514 Pill_Drop_Flag is set to FALSE then processing proceeds to step 516. At step 516, a determination is made whether any one of the following discretes is set to TRUE: Approach, the Approach_Flag, and the First_Pulse_Flag. If yes, processing proceeds to step 518 where Pulsetime is set to SHORT and First_Pulse_Flag is set to FALSE. Processing then proceeds to step 526.

If however, at step 516, no one of the discretes, i.e. Approach, the Approach_Flag, or the First_Pulse_Flag, is set to TRUE, then processing proceeds to step 520 where the value of Pulse_Count is reviewed. If Pulse_Count is greater than 4, then Pulsetime is set to LONG and Pulse_Count is set to 0 to restart the count. Processing then proceeds to step 526. If however, at step 520 Pulse_Count is not greater than 4, Pulsetime is set to MEDIUM and Pulse_Count is incremented at step 524 before proceeding to step 526. At step 526, the Motor discrete set to ON thereby turning on the pill tray electric motor to get the pill moving.

At step 528, the Pill_Drop_Flag status is checked to see if the drop optical sensor detected a pill. If the Pill_Drop_Flag is set to TRUE, this means that the pill has dropped out of the open end of the pill tray 302 and processing proceeds to step 532. However, if at step 528 Pill_Drop_Flag is set to FALSE then processing proceeds to step 530 where the Timeout counter is checked. If the Timeout counter is not zero at step 530, processing returns to step 506 to repeat the process until the drop optical sensor detects that the pill has dropped or the system times out, whichever occurs first. However, if at step 530 the Timeout counter is 0, then the system has timed out indicating a failure of a pill to drop within the specified time limit. The Status flag is set to "Failed" at step 534, the Pill_Drop_Flag is set to FALSE and the Motor discrete is set to OFF at 536, and processing terminates at 538.

At step 532, the Status flag is set to "Success" and processing proceeds to step 536 where the Pill_Drop_Flag is set to FALSE and the Motor discrete is set to OFF before processing terminates at 538.

Some embodiments in accordance to the present invention may be operated by configuring the controller using the input interface and the visual display to execute a specified pill setting and/or a specified dispensing schedule. A different type of pill is then loaded into each of at least one pill tray of the pill dispensing device. The pill dispensing device will then proceed to dispense pills into the transfer tray according to the specified pill setting and/or the specified dispensing schedule.

While the invention herein disclosed has been described by means of specific embodiments and applications thereof, numerous modifications and variations could be made thereto by those skilled in the art without departing from the scope of the invention set forth in the claims.

What is claimed is:

1. A pill dispensing device comprising:
   a base;
   a trough shaped pill tray with an open end and a closed end;
   a brush with flexible bristles extending towards said pill tray;
   at least one spring support coupling said base to said pill tray, wherein said at least one spring support is coupled to said pill tray at an off-perpendicular angle;
   a pill tray electric motor coupled to said pill tray and an offset weight;
   an approach optical sensor configured to detect whether a pill is at said open end of said pill tray; and
   a drop optical sensor configured to detect whether said pill detected by said approach optical sensor has dropped out of said open end of said pill tray.

2. The device of claim 1, wherein said trough shaped pill tray is configured to transition from a smaller cross-section at said open end to a larger cross-section at said closed end.

3. The device of claim 1, wherein said pill tray electric motor is configured to cause vibration of said pill tray.

4. The device of claim 1, further comprising an enclosure body coupled to said base, wherein said enclosure body comprises a hopper and a closable lid for said pill tray, and wherein said closable lid is coupled to said hopper.

5. A pill dispensing device comprising:
   abuse;
   a trough shaped pill tray with an open end and a closed end;
   at least one spring support coupling said pill tray to said base;
   a pill tray electric motor coupled to said pill tray;
   an enclosure body coupled to said base, wherein said enclosure body comprises a hopper and a closeable lid for said pill tray;
   a brush with flexible bristles coupled to said hopper, wherein said flexible bristles extend towards said pill tray;
   an approach optical sensor configured to detect presence of pills at said open end of said pill tray; and
   a drop optical sensor configured to detect whether a pill has dropped out of said open end of said pill tray.

6. The device of claim 5, wherein said pill tray electric motor is configured to cause vibration of said pill tray.

7. A pill dispensing device comprising:
   a base with a top surface and a bottom surface;
   a transfer tray assembly coupled to said top surface of said base;
   an enclosure body coupled to said base, wherein said enclosure body comprises at least one hopper and at least one closable lid;
   a controller; and
   at least one vibrating tray assembly coupled to said top surface of said base, wherein said vibrating tray assembly comprises:
   a pill tray with an open end and a closed end, wherein said open end is positioned above said transfer tray assembly and said pill tray is configured to handle pills of any shape and size, wherein each of said pill tray has a corresponding hopper and closable lid,
   a brush with flexible bristles coupled to said hopper, wherein said flexible bristles extend towards said pill tray;
   a spring support coupling said top surface of said base to said pill tray,
   an electric motor coupled to said pill tray and said controller,
   an approach optical sensor configured to detect presence of pills at said open end of said pill tray; and
   a drop optical sensor configured to detect whether a pill has dropped out of said open end of said pill tray.

8. The device of claim 7, wherein said pill tray is trough shaped and transitions from a smaller cross-section at said open end to a larger cross-section at said closed end of said pill tray.

9. The device of claim 7, wherein said electric motor coupled to said pill tray causes said pill tray to vibrate.

10. The device of claim 7, wherein said transfer tray assembly comprises:
    a trough shaped transfer tray with an open end and a closed end, said open of said transfer tray having a narrower cross-section than said closed end; and
    a transfer tray electric motor.

11. The device of claim 7, wherein said controller is selectively configured to cause said vibrating tray to dispense a selected number of pills into said transfer tray.

12. The device of claim 7, further comprising a visual display and an input interface.

13. The device of claim 7, wherein said controller is configured to store at least one pill setting, wherein each pill setting causes said controller to dispense a specified number of each of at least one type of pill.

14. The device of claim 7, wherein said controller is configured to store at least one dispensing schedule, wherein each dispensing schedule causes said controller to dispense a specified number of each of at least one type of pill at specific times and dates.

15. The device of claim 7, wherein said controller saves a record of pill count, dates, and times for each type of pill dispensed.

16. The device of claim 7, wherein said pill dispensing device is connected to a communication network for remote inputs of pill settings or dispensing schedules.

* * * * *